United States Patent
Machek et al.

(10) Patent No.: US 6,445,958 B1
(45) Date of Patent: Sep. 3, 2002

(54) STEERABLE CORONARY SINUS DEFIBRILLATION LEAD

(75) Inventors: James E. Machek, Roanoke, VA (US); Paul R. Spehr, Lake Jackson, TX (US)

(73) Assignee: Intermedics, Inc., Angleton, TX (US)

( * ) Notice: Subject to any disclaimer, the term of this patent is extended or adjusted under 35 U.S.C. 154(b) by 0 days.

(21) Appl. No.: 09/292,715

(22) Filed: Apr. 15, 1999

(51) Int. Cl.⁷ ................................................ A61N 1/05
(52) U.S. Cl. ...................................... 607/122; 607/119
(58) Field of Search ............................... 607/122–123, 607/115–116, 119; 600/372–374, 377, 381

(56) References Cited

U.S. PATENT DOCUMENTS

| | | | |
|---|---|---|---|
| 4,295,270 A | 10/1981 | Cammarata | 29/828 |
| 4,677,990 A * | 7/1987 | Neubauer | 607/119 |
| 4,898,577 A | 2/1990 | Bafger et al. | 604/53 |
| 4,922,927 A | 5/1990 | Fine et al. | 128/786 |
| 4,960,134 A | 10/1990 | Webster, Jr. | 128/786 |
| 4,976,689 A | 12/1990 | Buchbinder et al. | 604/95 |
| 5,005,587 A | 4/1991 | Scott | 128/786 |
| 5,007,434 A | 4/1991 | Doyle et al. | 128/772 |
| 5,030,204 A | 7/1991 | Badger et al. | 604/95 |
| 5,114,414 A | 5/1992 | Buchbinder | 604/95 |
| 5,170,803 A * | 12/1992 | Hewson et al. | 607/124 |
| 5,228,441 A * | 7/1993 | Lundquist | 600/380 |
| 5,360,441 A * | 11/1994 | Otten | 607/122 |
| 5,374,287 A | 12/1994 | Rubin | 607/131 |
| 5,376,074 A | 12/1994 | Buchbinder et al. | 604/96 |
| 5,476,498 A | 12/1995 | Ayers | 607/122 |
| 5,476,502 A | 12/1995 | Rubin | 607/127 |
| 5,487,757 A | 1/1996 | Truckai et al. | 607/122 |
| 5,545,200 A | 8/1996 | West et al. | 607/122 |
| 5,609,621 A | 3/1997 | Bonner | 607/122 |
| 5,626,602 A | 5/1997 | Gianotti et al. | 606/198 |
| 5,651,785 A | 7/1997 | Abela et al. | 606/15 |
| 5,782,239 A | 7/1998 | Webster, Jr. | 128/642 |
| 5,810,887 A * | 9/1998 | Accorti, Jr. et al. | 607/122 |
| 5,833,632 A * | 11/1998 | Jacobsen et al. | 600/585 |
| 5,911,725 A | 6/1999 | Boury | 606/108 |
| 5,935,102 A | 8/1999 | Bowden et al. | 604/95 |
| 5,984,957 A | 11/1999 | Laptewicz, Jr. et al. | 623/1 |
| 6,165,167 A | 12/2000 | Delaloye | 604/528 |
| 6,241,726 B1 | 6/2001 | Chia et al. | 606/41 |
| 6,308,091 B1 | 10/2001 | Avitall | 600/374 |

FOREIGN PATENT DOCUMENTS

EP   0709111   5/1996   ............ A61N/1/05

* cited by examiner

Primary Examiner—Kennedy Schaetzle
Assistant Examiner—Kristen Droesch
(74) Attorney, Agent, or Firm—Schwegman, Lundberg, Woessner & Kluth, P.A.

(57) ABSTRACT

An implantable defibrillation lead with steerable characteristics, allowing the lead to be more easily placed within the coronary sinus. The lead comprises an elongated lead body having a proximal end and a distal end. Adjacent the distal end, there is an electrode, preferably a coiled defibrillation electrode placed on the exterior of the elongated lead body. The distal end of the lead body has a permanent set or bend. A torque tube, extending through a lumen in the lead body from the proximal end of the lead to an anchor block adjacent the distal end of the lead, can be rotated by a physician to orient the bend in the lead. A cable passes through the torque tube from the proximal end of the lead through the anchor block to the distal end of the lead. This cable is affixed to a wall of the lumen, preferably in the direction of the bend. Pulling on the cable temporarily changes the bend in the distal end of the lead.

26 Claims, 3 Drawing Sheets

STEERABLE CORONARY SINUS DEFIBRILLATION LEAD

BACKGROUND OF THE INVENTION

1. Field of the Invention

The present invention relates generally to implantable cardiac stimulation devices and systems for regulating the contraction of a heart. More particularity, the invention relates to a defibrillation lead, and more particularly to a defibrillation lead having a steerable distal end.

2. Description of the Related Art

Implantable medical devices for treating irregular contractions of the heart with electrical stimuli are well known in the art. Some of the most common forms of such implantable devices are defibrillators and pacemakers.

Defibrillators are implantable medical devices used to treat fibrillation, a condition characterized by rapid, chaotic electrical and mechanical activity of the heart's excitable myocardial tissue that results in an instantaneous cessation of blood flow from the heart. Defibrillation is a technique employed to terminate fibrillation by applying one or more high energy electrical pulses to the heart in an effort to overwhelm the chaotic contractions of individual tissue sections and to restore the normal synchronized contraction of the total mass of tissue.

A pacemaker, or pacer, is an implantable medical device that delivers low energy electrical pulses to stimulate a patient's heart to beat at a desired rate in instances where the heart itself is incapable of proper self-regulation. This occurs when the heart's natural pacemaker, which causes the rhythmic electrical excitation of the heart and pumping of blood, malfunctions due to age or disease. Demand pacing is a process used to maintain normal beating of a heart having this condition.

Various types of leads for defibrillators and demand pacers have been suggested in the prior art. For example, large electrical patches sewn to the exterior surface of the heart have been used to deliver defibrillation pulses to the heart. Implantation of such patch electrodes requires opening of the patients chest during thoracic surgery. For pacing, pulses may be applied to the heart with the use of a pacer lead having an exposed metal surface, or demand pacer electrode, extending through a vein and into the heart.

Those involved in the medical arts recognized that prior art defibrillators required a high threshold level of energy for effective defibrillation, which limited the useful life-span of the devices and, more significantly, posed a significant risk of causing electrolysis of the blood and myocardial damage. It was realized that the defibrillation electrode configuration played an important role in the amount of energy needed to achieve successful defibrillation. This led to the development of transvenous defibrillation leads having long coil-shaped defibrillation electrodes for implantation into the right ventricle of the heart through a vein. For example, U.S. Pat. No. 4,922,927, the entire disclosure of which is incorporated herein by reference, discloses a defibrillation electrode made up of a plurality of separate wires wound side-by-side to form a tight coil. The coil was disposed upon an insulated tubular member and had a length sufficient to extend throughout the entire length of the ventricular chamber to provide sufficient electrode surface area for defibrillation.

Transvenous cardiac stimulation leads, such as the device of U.S. Pat. No. 4,922,927, also carry a demand pacing electrode. Thus, a single device implantable in one surgical procedure could provide defibrillation and pacing pulses for heart patients suffering from both irregular heart beat and, at times, cardiac fibrillation. This eliminated the need for multiple and complex surgical procedures to attach electrodes for both types of treatments.

Another defibrillation electrode configuration for use with dual purpose transvenous leads is disclosed in U.S. Pat. Nos. 5,476,502 and 5,374,287 to Rubin, which are also incorporated herein by reference in their entireties. The "Rubin" catheter included either a helical or lance shaped defibrillation electrode for delivering a defibrillation pulse directly to the interior of the septum of the patient's heart. The length of the helix-shaped electrode to be screwed into the septum from the right ventricle, about 0.5 cm to 1.0 cm, was substantially shorter than the conventional coiled transvenous defibrillation electrodes.

SUMMARY OF THE INVENTION

The characteristics and advantages of the present invention described above, as well as additional features and benefits, will be readily apparent to those skilled in the art upon reading the following detailed description and referring to the accompanying drawings.

We have invented a defibrillation lead with steerable characteristics, allowing the lead to be more easily placed within the coronary sinus. The lead of our invention comprises an elongated lead body having a proximal end and a distal end. At the proximal end there is an electrical connector. Adjacent the distal end, there is an electrode, preferably a coiled defibrillation electrode placed on the exterior of the elongated lead body. The distal end of the lead body has a permanent set or bend. A torque tube, extending through a lumen in the lead body from the proximal end of the lead to an anchor block adjacent the distal end of the lead, can be rotated by a physician to orient the bend in the lead. A cable passes through the torque tube from the proximal end of the lead through the anchor block to the distal end of the lead. This cable is affixed to a wall of the lumen, preferably in the direction of the bend. Pulling on the cable temporarily changes the bend in the distal end of the lead.

An important object of our invention is to provide a lead that can be directed into the coronary sinus of the heart.

Another important object of our invention is to provide a defibrillation lead which can be directed into the coronary sinus, using a bent distal end.

Another object of our invention is to provide a coronary sinus lead wherein the radial orientation of a bent distal lead can be controlled.

It is also an object of our invention to provide a lead having a torque apparatus for controlling the orientation of the distal of the lead. Another object of our invention is to provide the coronary sinus lead having a bent distal end wherein the degree of bending can be controlled.

These and other features and objects of our invention will be apparent to those skilled in the art from the following detailed description of our preferred embodiment, taking in connection with the accompanying drawings.

BRIEF DESCRIPTION OF THE DRAWINGS

For a detailed description of the preferred embodiments of the invention, reference will now be made to the accompanying drawings wherein.

DETAILED DESCRIPTION OF THE PREFERRED EMBODIMENTS

Figure 1:
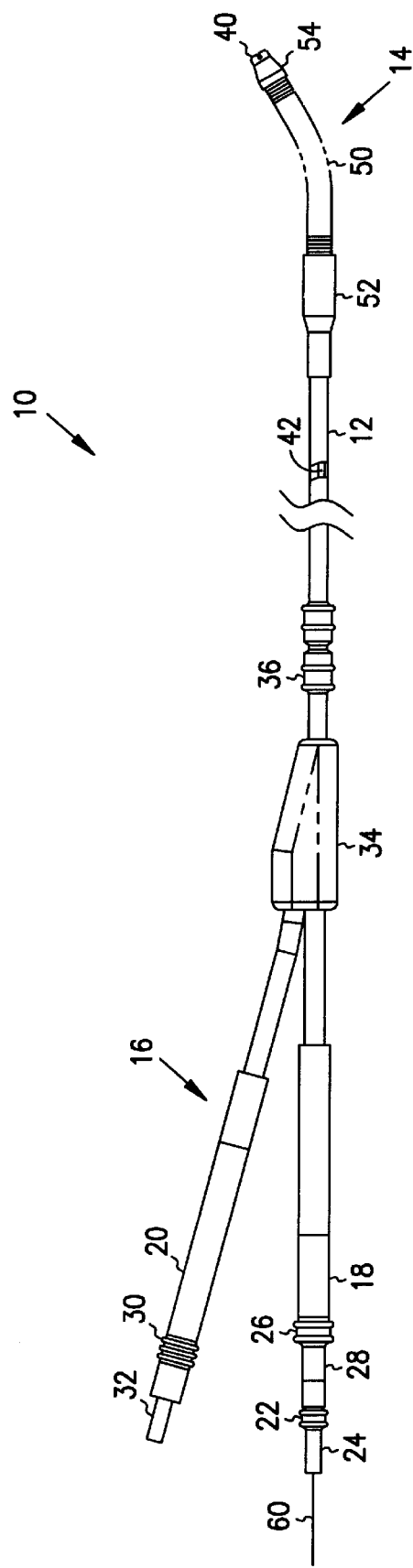
FIG. 1 is a perspective view of a steerable coronary sinus defibrillation lead according to the present invention.

The presently preferred embodiments of the invention are shown in the above-identified figures and described in detail below. In describing the preferred embodiments, like or identical reference numerals are used to identify common or similar elements. The figures are not necessarily to scale and certain features and certain views of the figures may be shown exaggerated in scale or in schematic form in the interest of clarity and conciseness.

Referring now to FIG. 1, a coronary sinus lead 10 is illustrated in perspective view. The coronary sinus lead 10 has an elongated lead body 12 having a distal end 14 and a proximal end 16. At the proximal end 16 there is an electrical connector 18, for example, an IS-1 connector for low voltage sensing at pacing functions, as is known in the art. There is also a high voltage electrical connector 20, preferably a DF-1 connector (Defibrillation-1). The IS-1 connector 18 has annular sealing rings 22 which isolate a pin connector 24 from body fluids when the connector is inserted into a header of an implantable cardiac stimulator of other device (not shown). Annular sealing rings 26 also isolate a ring connector 28 which may be provided if bipolar pacing or sensing is desired. The high voltage connector 20 also has annular sealing rings 30 which isolate a high voltage pin connector 32 in the same manner. The two connectors 18, 20 join at a junction protected by a boot 34. The lead 10 also has a suture sleeve 36 slidingly received on the elongated lead body.

Figure 2:
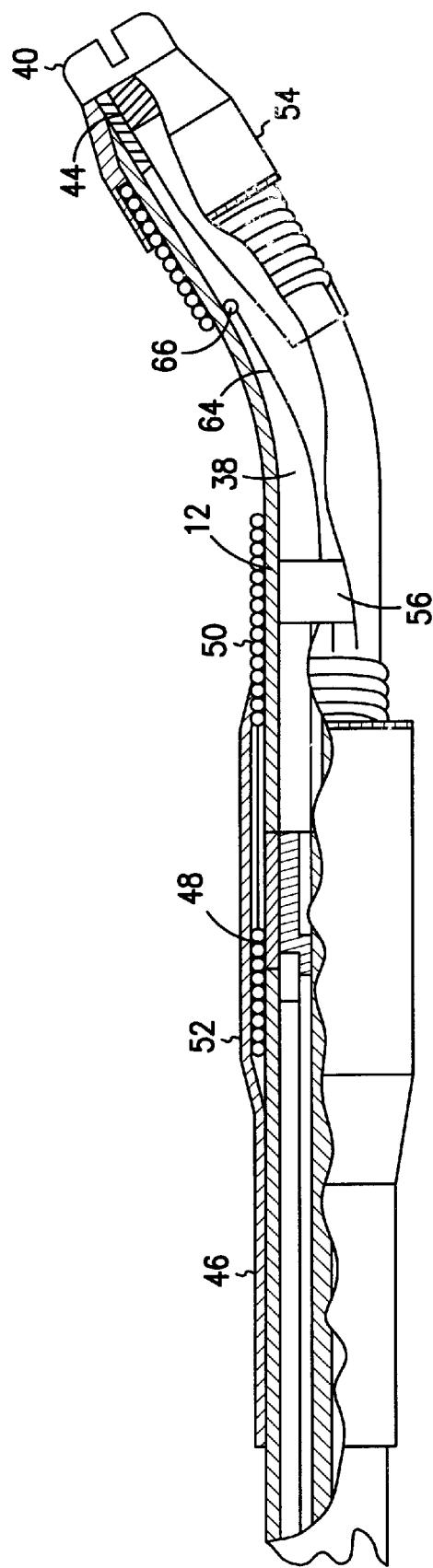
FIG. 2 is a partial through section of a distal end of the lead of FIG. 1.

As can be seen in FIG. 2, the lead body 12 defines a lumen 38 wherein various electrical conductors are carried from the proximal end of the lead to the distal end of the lead. For example, a low voltage pacing and sensing electrode 40 may be provided at the distal end of the lead and connected by a tri-filar conductor 44 to the pin connector 24 of the IS-1 connector. If bipolar pacing and sensing is desired an additional ring electrode 42, seen in FIG. 1, may be provided and similarly connected by a conductor (not shown) to the ring connector 28 of the IS-1 connector. In those applications where defibrillation capability is desired, a high voltage conductor 46 is also provided. The high voltage conductor 46 is connected through a crimp connector 48 through the wall of the elongated lead body 12 to a coiled defibrillation electrode 50. In our preferred embodiment, the coiled defibrillation electrode 50 is placed at the distal end of the lead body. That portion of the lead body underlying the coiled electrode 50 is given a permanent bend by heat setting the polymer of the lead body. This makes the distal end of the lead body tend to assume a bent shape, preferably assuming an angle of about 45° from an axis of the lead body if the lead were straightened. A proximal sleeve 52 protects a proximal end of the coiled electrode 50 while a distal sleeve 54 performs a similar function at the distal end of the coiled electrode.

Figure 3:
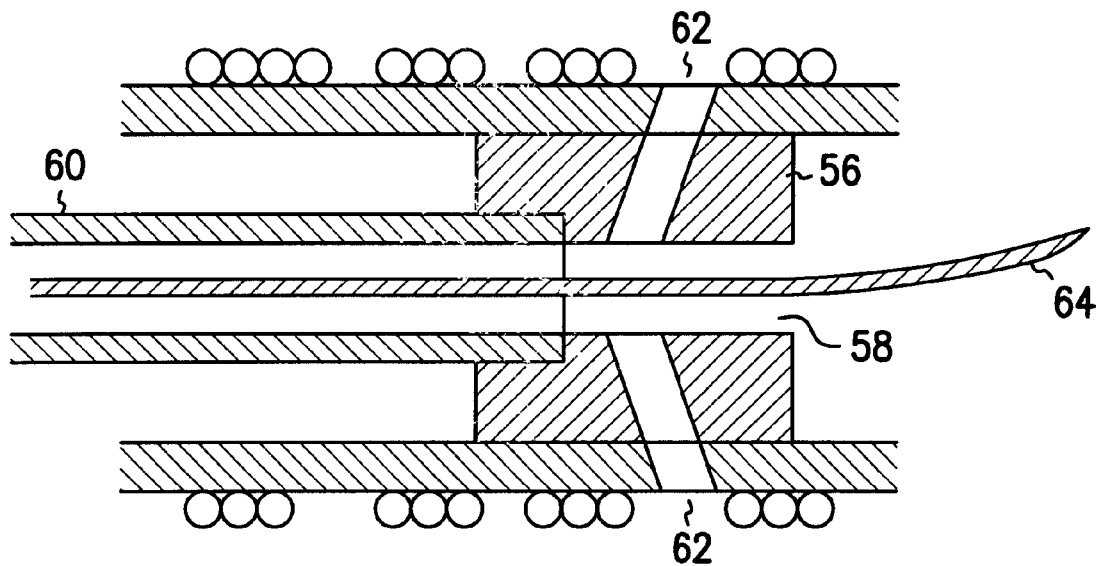
FIG. 3 is an enlarged through section illustrating an anchor block within the distal end of the lead.
Figure 4:
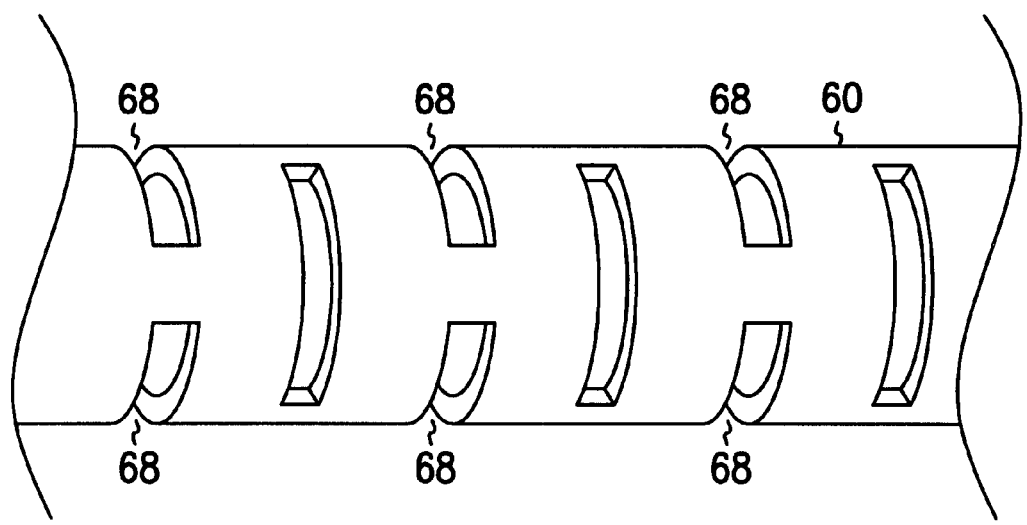
FIG. 4 is a perspective view of a portion of a torque tube.

Within the lumen 38 of the lead body 12 there is an anchor block 56, placed preferably at the distal end of the lead, just proximal from the bend in the lead. The anchor block 56 has a central through bore 58 which can be seen most easily in FIG. 3. A torque transmitting member, preferably a torque tube 60, is affixed to the anchor block 56 and the anchor block itself is affixed to the inner wall of the lead body. The torque tube 60 extends from the anchor block 56 to the proximal end of the lead. Orifices 62 are provided through the anchor block 56 and through the wall of the lead body 12. Steroids or other medicines may be selectively passed through the torque tube 60 and exuded through the orifices to reduce reaction to the placement of the lead, or to provide other medical benefits. This occurs best if the torque tube 60 is a solid wall structure. The wall of the torque tube may be comprised of nickel-titanium alloy, e.g., Nitinol metal, or a suitable material such as polyamide. In the alternative, more flexibility may be provided in the torque-tube 60 by providing partially circumferential slots 68 as shown in FIG. 4. At a given circumference two slots are provided, each slot being less than 180°, thus providing a small connecting segment between the two slots on either side of the tube. An adjacent circumference would have similar slots, with the connected portions offset by 90°. Such a structure provides for increased flexibility while still allowing the torque tube to transmit rotational forces from the proximal end of the lead body to the distal end.

A filament, preferably a cable 64, is extended through the torque tube 60 from the proximal end of the lead body through the anchor block 56 to the distal end of the lead body. The cable is preferably comprised of nineteen strands of 0.001 inch (0.0024 cm) diameter wire of MP35N stainless steel. The cable 64 is secured to the wall of the lead body at a fixture 66. This fixture is preferably located on the side of the lead body in the direction of the bend, that is, along the smallest radius of bending of the bend. Pulling on the cable 64 will cause the distal end of the lead body to bend more, allowing for the bend in the distal end to be increased. This provides an additional degree of freedom for manipulating the distal end of the lead. In our preferred embodiment, the bent distal end of the lead, which includes the defibrillation shock coil, comprises about three to four centimeters from the distal electrode 40.

To radially manipulate the bend, the torque tube 60 is connected to the pin connector 24. In our preferred embodiment, the pin connector is rotatable with respect to the lead body. Pin connectors of this kind are known in the art, being used to apply torque to coiled wires which act to expose sharpened helical coils or "cork screws" at the distal end of the lead. Such a lead was marketed by Osypka GmbH as the "PY" lead. The torque tube described herein permits relatively more torque to be transferred to the distal end of the lead, thus allowing the bent distal end to be directed radially. The electrical connection between the pin connector and an electrode near the distal end of the lead may be made through the torque tube, but is more preferably made, in whole or in part, through a coil conductor.

Those skilled in the art will recognize from the foregoing description that our invention can be used in cardiac leads in other configurations without departing from the teachings of our invention. While preferred embodiments of the present invention have been shown and described, modifications thereof can be made by one skilled in the art without departing from the spirit or teachings of this invention. The embodiments described herein are exemplary only and are not limiting. Many variations and modifications of this system and apparatus are possible and are within the scope of the invention. Accordingly, the scope of protection is not limited to the embodiments described herein, but is only limited by the claims which follow, the scope of which shall include all equivalents of the subject matter of the claims.

What is claimed is:

1. An implantable cardiac stimulation lead comprising an elongate lead body having a proximal and a distal end and an interior surface forming a lumen extending through said elongate lead body, said lead body having a preformed, permanent bend therein;
an electrical connector at said proximal end;
a first electrode near said distal end,
an electrical conductor electrically connecting said electrical connector and said electrode, and
a flexible filament slidingly received in said lumen and extending from said distal end of said lead body to said proximal end, said filament being secured to an interior wall of said lead body at said distal end.

2. The implantable cardiac stimulation lead according to claim 1 wherein said filament is a cable.

3. The implantable cardiac stimulation lead according to claim 1 wherein said electrode comprises a coil defibrillation electrode disposed on said lead body.

4. The implantable cardiac stimulation lead according to claim 1 further comprising an elongate torque-transmitting member fixedly coupled to said lead body.

5. The implantable cardiac stimulation lead according to claim 1 wherein said bend is adjacent said distal end of said lead body and wherein said filament is secured to said interior wall distal to said bend and adjacent an inside radius of said bend.

6. The implantable cardiac stimulation lead according to claim 5 wherein said bend is about 45 degrees.

7. The implantable cardiac stimulation lead according to claim 5 wherein said electrode comprises a coil defibrillation electrode disposed on said lead body.

8. An implantable cardiac stimulation lead comprising an elongate lead body having a proximal and a distal end and an interior surface forming a lumen extending through said elongate lead body;
an electrical connector at said proximal end;
a first electrode near said distal end;
an electrical conductor electrically connecting said electrical connector and said electrode;
a filament slidingly received in said lumen and extending from said distal end of said lead body to said proximal end, said filament being secured to an interior wall of said lead body at said distal end;
a torque tube coupled with the lead body; and
said lead body has a preformed, permanent bend adjacent said distal end of said lead body and wherein said filament is secured to said interior wall distal to said bend and adjacent an inside radius of said bend.

9. The implantable cardiac stimulation lead according to claim 8 wherein said bend is about 45 degrees.

10. The implantable cardiac stimulation lead according to claim 8 wherein said electrode comprises a coil defibrillation electrode disposed on said lead body.

11. An implantable cardiac defibrillation lead comprising an elongate lead body having a proximal and a distal end and an interior surface forming a lumen extending through said elongate lead body, said lead body having a bend therein adjacent said distal end;
a means for bending the distal end of the lead body while the lead body is implanted within a body;
an anchor block disposed adjacent said distal end of the lead body;
a torque tube coupled with the anchor block, the torque tube including two or more partially circumferential slots;
an electrical connector at said proximal end;
a coil defibrillation electrode disposed on said lead body near said distal end, at least part of said electrode enclosing said bend, and
an electrical conductor electrically connecting said electrical connector and said electrode.

12. The implantable cardiac stimulation lead according to claim 11 wherein the means for bending is controllable from the proximal end of the lead body.

13. The implantable cardiac stimulation lead according to claim 11 wherein and each said circumferential slot extends less than 180 degrees around a circumference of the tube.

14. An implantable cardiac stimulation lead comprising an elongate lead body having a proximal and a distal end and an interior surface forming a lumen extending through said elongate lead body, said lead body having a bend therein adjacent said distal end;
an electrical connector at said proximal end;
a first electrode near said distal end,
an electrical conductor electrically connecting said electrical connector and said electrode,
an anchor block adjacent said distal end of said lead body, and proximal to said bend, and
an elongate torque-transmitting member fixedly coupled to said anchor and extending through said lumen to said proximal end of said elongate lead body.

15. The implantable cardiac stimulation lead according to claim 14 wherein said bend is about 45 degrees.

16. The implantable cardiac stimulation lead according to claim 14 further comprising a filament slidingly received in said lumen and extending from said distal end of said lead body to said proximal end, said filament being secured to an interior wall of said lead body at said distal end.

17. The implantable cardiac stimulation lead according to claim 16 wherein said filament is a cable.

18. The implantable cardiac stimulation lead according to claim 14 wherein said torque-transmitting member comprises a tube.

19. The implantable cardiac stimulation lead according to claim 18 wherein said tube is connected distally to at least one orifice communicating between the interior of said tube and the outside of said lead body.

20. The implantable cardiac stimulation lead according to claim 18 wherein said tube has a plurality of partially circumferentially disposed slots therein.

21. The implantable cardiac stimulation lead according to claim 18 wherein said tube is comprised of nitinol.

22. The implantable cardiac stimulation lead according to claim 18 wherein said tube is comprised of polyamide.

23. The implantable cardiac stimulation lead according to claim 18 further comprising a filament slidingly received in said tube and extending from said distal end of said lead body to said proximal end and through said anchor block, said filament being secured to an interior wall of said lead body at said distal end.

24. The implantable cardiac stimulation lead according to claim 23 wherein said filament is secured to an interior wall distal to said bend and adjacent an inside radius of said bend.

25. The implantable cardiac stimulation lead according to claim 23 wherein said filament is a cable.

26. The implantable cardiac stimulation lead according to claim 25 wherein said electrode comprises a coil defibrillation electrode disposed on said lead body.

* * * * *

UNITED STATES PATENT AND TRADEMARK OFFICE
CERTIFICATE OF CORRECTION

PATENT NO.      : 6,445,958 B1
DATED           : September 3, 2002
INVENTOR(S)     : James E. Machek and Paul R. Spehr It is certified that error appears in the above-identified patent and that said Letters Patent is hereby corrected as shown below:

<u>Title page,</u>
Item [56], References Cited, U.S. PATENT DOCUMENTS,
Delete "4,677,990" and insert -- 4,667,990 --, therefor.
Delete "11/1998" and insert -- 10/1998 --, therefor.

<u>Column 6,</u>
Line 12, delete "and" (next to wherein).

Signed and Sealed this

Tenth Day of December, 2002

JAMES E. ROGAN
*Director of the United States Patent and Trademark Office*